United States Patent [19]

Richardson et al.

[11] Patent Number: 4,669,836

[45] Date of Patent: Jun. 2, 1987

[54] PHOTOREFRACTOR OCULAR SCREENING SYSTEM

[75] Inventors: John R. Richardson, Huntsville; Joseph H. Kerr, Wedowee, both of Ala.

[73] Assignee: The United States of America as represented by the Administrator of the National Aeronautics and Space Administration, Washington, D.C.

[21] Appl. No.: 655,605

[22] Filed: Sep. 28, 1984

[51] Int. Cl.⁴ .......................... A61B 3/14; G03B 29/00
[52] U.S. Cl. ..................................... 351/206; 354/62; 351/208
[58] Field of Search ...................... 351/206, 208, 214; 354/62

[56] References Cited

U.S. PATENT DOCUMENTS

| | | | |
|---|---|---|---|
| 3,388,646 | 6/1968 | Sullivan | 351/206 X |
| 3,944,342 | 3/1976 | Martinez | 351/214 |
| 4,208,107 | 6/1980 | Oharek | 351/221 X |
| 4,304,483 | 12/1981 | Whitten | 351/206 X |
| 4,394,074 | 7/1983 | McMahon | 351/206 |
| 4,523,820 | 6/1985 | Kaakinen | 351/206 |

Primary Examiner—Rodney B. Bovernick
Attorney, Agent, or Firm—Joseph H. Beumer; John R. Manning; Leon D. Wofford, Jr.

[57] ABSTRACT

The invention relates to a method and apparatus for detecting human eye defects, particularly detection of refractive error. The invention operates by recording on color film the eye reflex which occurs when eyes are exposed to a flash of light. The photographs are compared with predetermined standards, to detect eye defects. As shown in FIGS. 1 and 2, the base structure of the ocular screening system (10) is folding interconnect structure (12), comprising hinged sections (14), (16), and (18). Attached to one end of structure (12) is head positioning station (24) which comprises vertical support (26), a head positioning bracket (28) having one end attached to the top of support (26), and two head positioning lamps (33) to verify precise head positioning. At the opposite end of interconnect structure (12) is a camera station (34) with camera (38), electronic flash unit (44), and blinking fixation lamp (46), for photographing the eyes of persons being evaluated.

6 Claims, 15 Drawing Figures

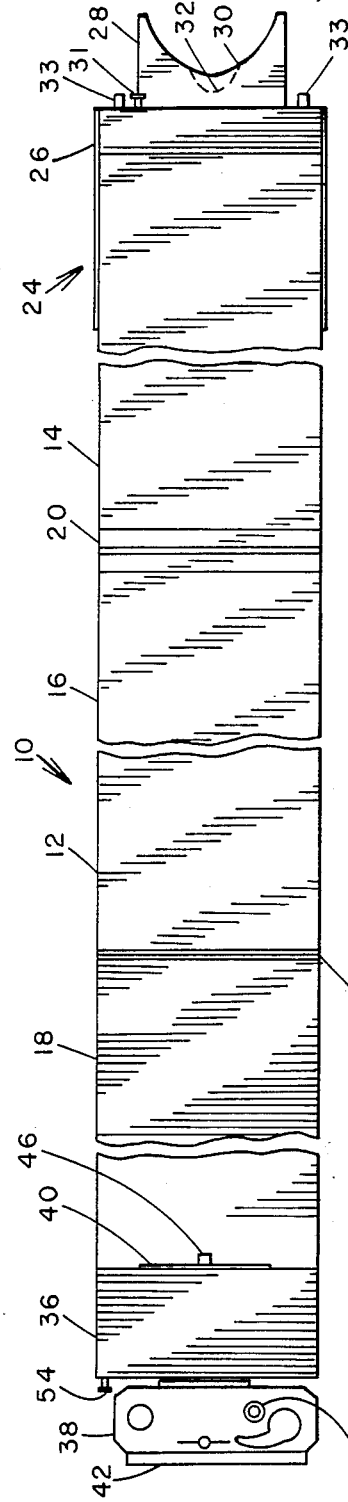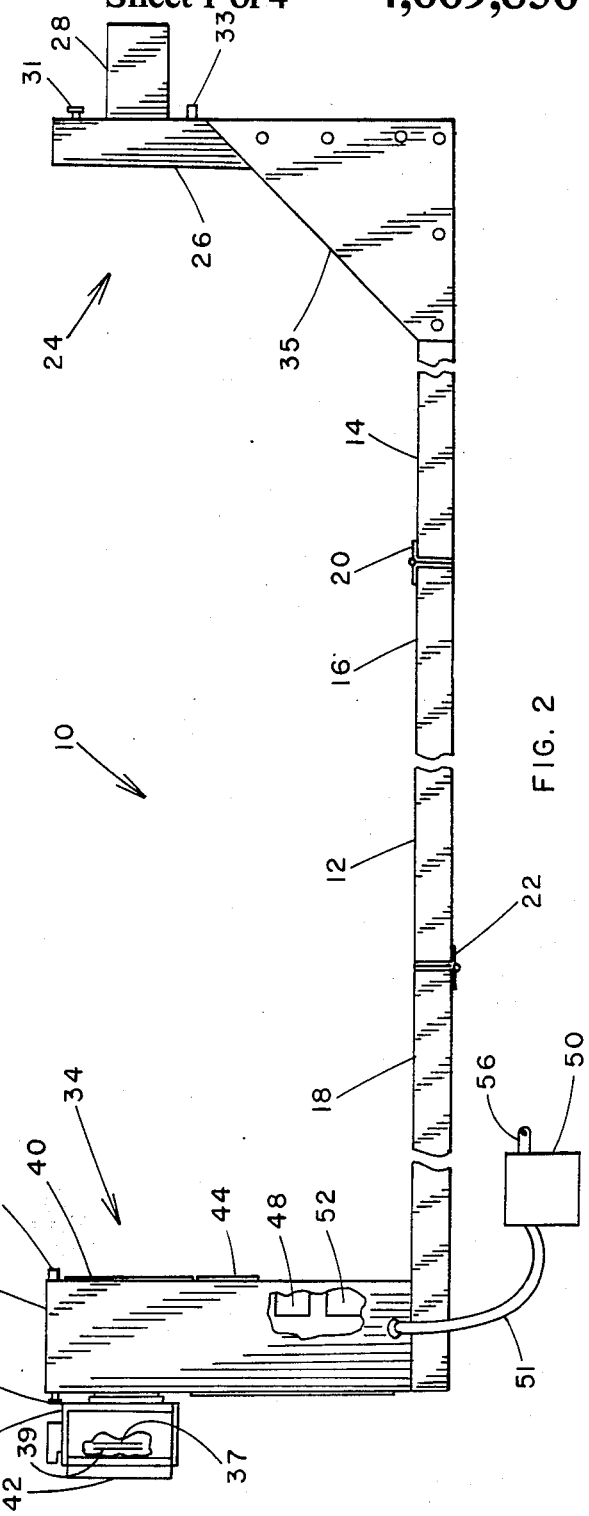

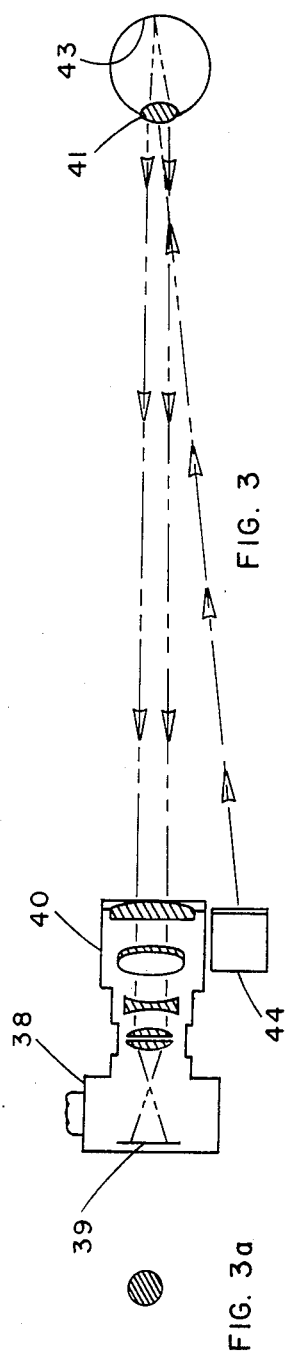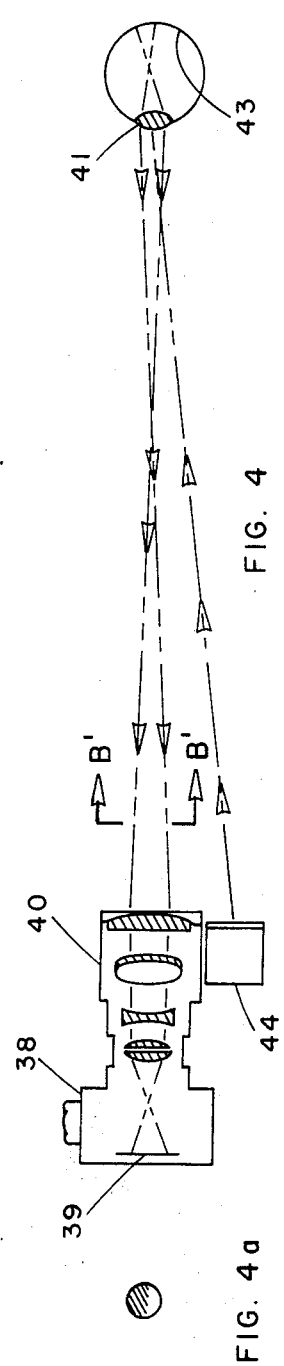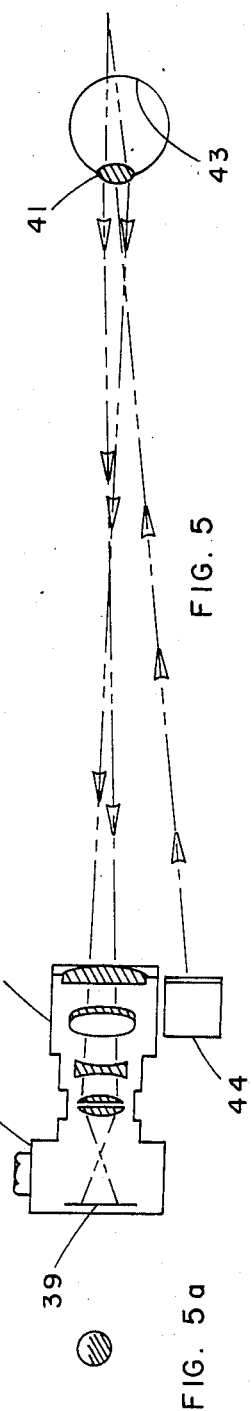

PHOTOREFRACTOR OCULAR SCREENING SYSTEM

ORIGIN OF THE INVENTION

The invention described herein was made in the performance of work under a NASA contract and is subject to the provisions of Public Law 96-517 (94 Stat 3019; 35 USC 200-211).

TECHNICAL FIELD

The present invention relates generally to a method and apparatus for detecting eye defects and more specifically to a method and apparatus for detection of refractive error and other diseases of the human ocular system by photorefraction.

BACKGROUND OF THE INVENTION

For a long time, the primary way of measuring visual acuity has been through the use of a Snellen visual acuity chart or "E-chart." This involves a test chart with a series of letters in the alphabet such as L, D, O, N, and E, which are very large at the top of the chart and decrease in size to the bottom of the chart. The person being tested stands 20 feet from the chart and covers one eye and is asked to read the letters on a given line on the chart. A person able to read the bottom line has a 20/15 visual acuity. A person who can read only the largest letters has a poor visual acuity of about 20/300. Both eyes are tested in this manner. The disadvantage of the Snellen visual acuity test is that it requires the cooperation of the subject being tested and the letters can be memorized. Young infants and children less than 3 years old cannot be tested with the "E" chart. The Snellen test will not detect strabismus (ocular alignment) or lens obstructions, such as cataracts or tumors.

Since the invention of the retinascope by Cuignot in 1873, it has been possible to assess the refractive state of the eye by observing the refraction of light rays from the retina. In retinascopy, the source light, point of observation, and the subject's eye are approximately collinear. The refractive state is generally determined by moving the source light and adjusting the power of a spectacle lens in front of the eye so as to cancel the apparent motion of the source light on the retina by making the peephole of the retinascope conjugate with it.

One prior art method is described in the University of Helsinki publication *ACTA Ophthalmologia*, volume 57, 1979. The article is entitled "A Simple Method for Screening of Children with Strabismus, Anisometropia or Ametropia by Simultaneous Photography of the Corneal and the Fundus Reflexes" by author Kari Kaakinen. This article presents a simple screening method for detecting strabismus, anisometropia, and ametropia in young children by simultaneous photography of the corneal and fundus reflexes with a conventional camera and flashlight. In this article Mr. Kaakinen demonstrated off-axis photo refraction for detecting strabismus and refractive error at one meter. One disadvantage to Mr. Kaakinen's system is that it does not appear to be able to detect refractive error between 2.0 diopters myopic and 1.3 diopters hyperopic. The system lacks sensitivity in the 0.75 to 1.3 diopter range. The retinal reflex fundus images are small because of the 55 millimeter lens. His system requires the use of cyclopegic agents to dilate the pupils for optimum results. This makes the system more difficult to use because cyclopegic agents can only be administered by a doctor. The Kaakinen System does not use an integral head positioning station.

A second prior art method is described in the *Journal of the Optical Society of America*, February 1974 (volume 64, No. 2). This article is entitled "Photorefraction: A Technique for Study of Refractive State at a Distance" by Howard C. Howland and Bradford Howland. In this article, Howard C. Howland and Bradford Howland demonstrated a special segmented photorefraction attachment with an integral fiber optic light guide mounted in the center of the attachment. This technique does not provide a picture of the fundus reflex but does show a star arm pattern that increases with dioptric error. The Howland and Howland system also uses a 55 millimeter lens. The system is more complex, does not use color film and does not have its head positioning station integrated with the camera system. No retinal reflex image analysis for strabismus, lens obstructions, or pupil size differences can be performed with this system.

An early experimental system was developed previously by the National Aeronautics and Space Administration at Marshall Space Flight Center, Alabama, working jointly with Electro-Optics Consultants, Inc., under a NASA contract. A 6.4 m phototype off-axis photorefractor system was developed under the NASA contract with E.O.C. This system used a 1000 mm f/11 Celestron ® lens. The system had several deficiencies. (1) Image resolution was poor because of a combination of using the lens at its minimal focal point (short depth-of-field) and the use of ASA 400 high speed color slide film. (2) The camera station was independent of the head positioning station. (3) The system required a room long enough to provide 25 feet of unobstructed floor space and a permanent or semi-permanent set-up for operation, which required a special alignment procedure and made the system non-portable. (4) Photographs made with this system produced a large corneal reflection (a reflection of the flash from the outer surface of the eye), which took the form of a bright white circle obscuring up to 9% of the surface area (with a 6 mm pupil) of the retinal reflex image. (5) Refractive error indications were exaggerated; in some cases where minimum refractive error was indicated in the image, none could be found by ophthalmalogical examination.

The 6.4 m MFSC/EOC system also exhibited several problems. The depth-of-field of the 1000 mm lens focused at 6.4 m was approximately less than 13 mm. In order to obtain a decent film exposure using the f11 lens requires the use of high speed (ASA 400) color film which resulted in grainy images. The combination of lens focal distance and film resulted in minimally acceptable retinal reflex image quality. Another major deficiency of the system involved installation, requiring 7.6 m of unobstructed floor space, of two separate components, the camera and head positioning stations which required special alignment procedures to assure satisfactory system operation.

From the above it may be seen that none of the prior art systems provide a really quick and accurate way of detecting eye defects. Moreover, the Howland and Howland method is not readily capable of adequately screening infants or other noncommunicative persons for amblyopia, a conditon of poor vision even with the use of corrective glasses. Untreated, amblyopia can result in vision degradation, perhaps even total blindness. Children should be screened frequently for amblyopia, but screening programs have not been instituted in the United States due to a lack of a simple, reliable, fast, and relatively inexpensive method.

Therefore, it is an object of our invention to provide a method and apparatus for detecting eye defects which is simple, quick, accurate, and relatively inexpensive.

It is another object of our invention to provide a method and apparatus for detecting eye defects which does not require a permanent examination room or highly trained personnel to perform the screening operation.

It is a further object of our invention to provide a method and apparatus for detecting eye defects which does not require the subject of the examination to use cyclopegic agents or to do anything else except to look at a fixation light located near the lens of the camera.

It is a still further object of our invention to provide a method and apparatus for detecting eye defects which can isolate amblyopia and pre-amblyopic conditions and is also useful in detecting other eye diseases in their formative stages and in evaluating treatments.

SUMMARY OF THE INVENTION

The present invention is a method and apparatus for detecting eye defects by recording on color film the eye reflex which occurs when human eyes are exposed to a flash of light. The invention, which is a photorefractor ocular screening system, comprises: an interconnect structure comprising an elongated beam; a head positioning station attached to one end of said interconnect structure, for positioning the head of a person whose eyes are being evaluated; and a camera station attached to the other end of said interconnect structure, for photographing the eyes of the person whose eyes are being evaluated, for purposes of detecting eye defects.

The method of evaluating human eyes in order to discover eye defects or eye abnormalities comprises: stationing a person whose eyes are to be evaluated at a head positioning station; positioning the head of said person in a head positioning hood and facing in a predetermined direction; placing a camera at a camera station a predetermined distance in front of the eyes of said person with said camera facing toward the face of said person; simultaneously operating an electronic flash unit and the shutter of said camera in order to expose a film so as to image the eyes of said person; developing and printing said film in order to produce a photograph of the fundus reflex from the eyes of said person; and comparing said photograph with several predetermined empirical standards to determine if any one of several known indicators of eye defects is present in said photograph.

BRIEF DESCRIPTION OF THE DRAWINGS

FIG. 1 is a plan view of the photorefractor ocular screening system of the invention.

FIG. 2 is a side view of the ocular screening system shown in FIG. 1.

FIG. 3 is a diagram illustrating how the ocular screening system detects an emmetropic eye condition.

FIG. 4 is a diagram illustrating how the ocular screening system detects a myopic eye condition.

FIG. 5 is a diagram illustrating how the ocular screening system detects a hyperopic eye condition.

FIG. 6a shows emmetropic eyes.

FIG. 6b shows eyes with myopia.

FIG. 6c shows eyes with hyperopia.

FIG. 6d shows eyes with anisometropia.

FIG. 6e shows eyes displaying fragmented retinal pattern.

FIG. 6f shows eyes having one lens obstruction.

FIG. 6g shows eyes displaying a strabismus condition.

DETAILED DESCRIPTION OF THE INVENTION

Figure 6A:
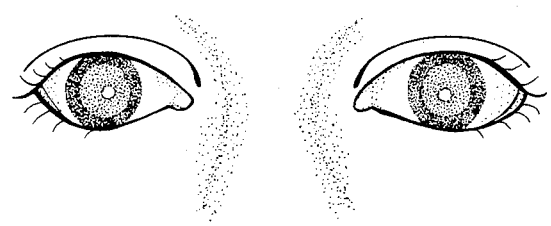
FIGS. 6a to 6g illustrate various eye conditions, both normal and abnormal, which may be detected using the method and apparatus of the invention.

The present invention is a quick and accurate method of detecting eye defects. It is particularly useful in screening infants and other noncommunicative persons for refractive error and other ocular defects including amblyopia, a condition causing poor vision, even when corrective lenses are used.

Looking now at FIGS. 1 and 2, there is shown the ocular screening system, designated generally by numeral 10. The base structure for the entire ocular screening system 10 is a folding interconnect structure 12. The interconnect structure 12 is designed to be horizontal when system 10 is set up in operating position and to rest on a table or other support. Structure 12 is a long, narrow, hollow beam, preferably of box-beam construction, having three sections, 14, 16, and 18 hinged together end-to-end. Sections 14 and 16 are connected by hinge 20. Sections 16 and 18 are connected by hinge 22.

Attached to the end of section 14 is a head positioning station 24 comprising a thin vertical support 26, mounted at a right angle to section 14. Attached near the top of vertical support 26 and extending out horizontally from support 26 is a flat, elongated head positioning hood 28. The unsupported end of head positioning hood 28 has a semicircular concave cut-out 30 designed to fit around a person's face and to frame his eyes. The lower side of bracket 28 has an additional cut-out 32, adjacent to the center of cut-out 30, to accommodate a person's nose, when his forehead is pushed into cut-out 30. Two head positioning lamps 33 are mounted on vertical support 26 to verify precise head positioning and are controlled by switch 31. In order to strengthen the structure and restrain any forward movement of the head positioning station 24, triangular-shaped angle braces 35 are mounted at the junction of section 14 and vertical support 26.

The head positioning lamps 33 used in the preferred embodiment of the invention are 1 watt red lamps, controlled by switch 31 which is preferably spring loaded and normally open. Lamps 33 are preferably red, but may be other colors, such as blue, green, or amber. (White lamps would not work well in this application because of the fact that they would cause a subject's eye pupils to close after they had been dilated (opened) by several minutes of exposure to a darkened room.) Head positioning lamps 33 are positioned so that they will be below the nose and cheeks of a person whose head is in head positioning hood 28. The operator at the head positioning station pushes switch 31 to switch on head positioning lamps 33 to see if the person's head is positioned well in the head positioning hood 28 for optimum location of the eyes. When lamps 33 are lit, the head positioning operator looks at the front of the subject's face to see if any appreciable amount of light is shining upward around the sides of his nose and particularly around his cheeks. If so, his head is improperly positioned and the operator pushes his head further into the head positioning hood 28.

At the opposite end of interconnect structure 12 and attached to the end of section 18 is a camera station 34 comprising vertical support 36, which is somewhat thicker than previously described vertical support 26. Camera 38, preferably a 35 mm type, is mounted to lens 40, which is attached to support 36 by means of brackets (not shown). The camera and lens are aligned to face toward head positioning station 24. Camera 38 is preferably equipped with a shutter 37, film plane 39, a telemacro lens 40, (which extends through support 36), and a data back 42. Just below lens 40, electronic flash unit 44 is mounted by brackets (not shown) in vertical support 36, also facing head positioning station 24. Just above lens 40, at the top of vertical support 36, is mounted a fixation lamp 46. Lamp 46 blinks at a frequency of about 1 Hertz per second to provide a fixation target upon which the subject's eyes may focus. The blink frequency for lamp 46 is controlled by oscillator circuit 48, which is mounted on support 36, directly below flash unit 44. Power for the system is provided by an external DC power supply 50 connected to terminal board 52 by cable 51. Power supply 50 plugs into a 110 V AC source (not shown) by use of prongs 56 attached to the case of power supply 50. Terminal board 52 is mounted in vertical support 36, below oscillator 48. When switch 54 is on, board 52 distributes power to recharge the electronic flash unit 44 and operate the fixation lamp 46 and the head positioning lamps 33 located on the head positioning station 24. From the above, it may be seen that the centerline of camera 38 and the centerline of head positioning hood 28 are on the same optical axis. Although either black and white or color film may be used in camera 38, color film is preferably used and optimum results are achieved with the color film.

Data back 42 is a commercially available device attached to the back of camera 38. It provides a sequential numbering system for each frame of a film roll used in camera 38. As each frame (or individual photograph) is exposed, the next number is automatically displayed by an LCD display on the back of data-back 42. The same number is automatically imprinted on the film so that, after the film is developed, this number will appear in the lower right hand corner of the negative. In practice, the operator at the camera station calls the number to the person logging names and personal information at the head positioning station.

In the development of this photorefractor ocular screening system, considerable time and experimentation has been devoted to choosing a lens system which provides optimum results in terms of image size, resolution, and depth of field. The lens finally chosen for the 2.4 meter prototype of the invention is a Tamron ®, 500 mm, f/8, tele-macro, catadioptric lens, which provides a large depth of field, when focussed at 2.4 meters. To achieve the proper results, it was discovered that a tele-macro lens was needed, to provide close-up photographs at the 2.4 meter distance and capable of focussing to a much shorter focal length. The particular catadioptric lens used is capable of both refraction and reflection of light with a particular lens arrangement having a four-element lens between the main mirror and the front mirror, to increase the resolution power of the lens system.

The camera 38, camera lens 40, camera data-back 42, and the flash unit 44, which were incorporated in the prototype of this ocular screening system, are all available commercially. The camera is a Nikon ® model FG 35 mm camera. The data-back is a Nikon ® model MF15. The lens is a Tamron ®500 mm, f/8, tele-macro, catadioptric type, manufactured by the Tamron Company Ltd. of Tokyo, Japan. The flash unit is a Sunpak ® model 333, manufactured by the Sunpak Division of Berkey Marketing Companies of Woodside, N.Y. The film used in the camera 38 is preferably Kodak ®VR200, a fine-grained color film which produces excellent resolution in this application.

The invention 10 may be folded up in its compact position for storage or traveling by folding the interconnect structure 12 so that its three sections 14, 16, and 18 lie flat against each other. In the folded position, section 18 lies on top of section 16 which in turn lies on top of section 14. With interconnect structure 12 folded in this manner, camera station 34 is adjacent to head positioning station 24. Thus, the screening system 10 when folded occupies only about one-third of its regular length when it is in the operating position. The system 10 may be unfolded and put back into its operating position by simply unfolding interconnect structure 12 to its full length.

To operate the system, first unfold the structure if necessary. A person whose eyes are to be evaluated is placed in a darkroom for a minimum of 3 minutes prior to being photorefracted, in order to dilate the person's eyes. The person is then positioned at the head positioning station 24 with his head in the head positioning hood 28. The operator of the system then takes a position adjacent to the camera station 34. Operation of switch 54 energizes the curcuit of the electronic flash unit 44, the fixation lamp 46 and the two head positioning lamps 33. Operation of the shutter release 55 (FIG. 1) causes the camera shutter 37 to open and the electronic flash 44 to fire, thus illuminating the subject's eyes. The appearance of the eyes, particularly the formation of a light crescent in either the upper or the lower fundus reflex images, is compared with several predetermined standard indicators, as determined from photographs previously taken, to ascertain what defects, if any, are present in the subject's eyes.

To describe the theory of operation of the device, attention is directed to FIG. 3. The light from the off-axis electronic flash unit 44 enters the subject's eye where it passes through the lens 41, of the eye, strikes the retina 43, and is reflected back toward the camera lens assembly 40. If the eye is focused at the plane of the forward portion of camera lens 40, light from electronic flash unit 44 illuminates a very small area of the retina 43. The light is reflected from the retina 43, through the camera lens 40 and into the film plane (at 39) as a reddish-colored fundus reflex, which, in this case, is emmetropic or "normal." FIG. 3a shows a fundus reflex for "normal" eyes.

Looking now at FIGS. 4 and 5, the conditions for myopia (nearsightedness) or hyperopia (farsightedness), respectively, are shown. As may be seen in these diagrams, when the eye is focused on fixation lamp 46 (FIG. 2) light rays travel in parallel lines to the lens 41 of the eye where they are bent so as to focus on the retina 43 at the rear of the eyeball. However, myopic eyes focus in front of the retina 43, as in FIG. 4, and hyperopic eyes focus behind the retina 43, as in FIG. 5. Both conditions cause blurred eyesight, which needs correction.

FIG. 4 shows the condition for a myopic (nearsighted) eye (or a normal eye focused at a point in front of the camera). Here the light from the off-axis electronic flash forms a circle of appreciable size on the retina 43. That retinal image is conjugate with an image in the same plane B'—B' between the subject and the camera lens. Hence rays from the retina return to form a larger circle of light, (FIG. 4) than was generated by the normal eye in FIG. 3. The light is, in turn, imaged on the film plane 39, showing a light colored crescent at the bottom portion on the fundus reflex (see FIG. 4a). The hyperopic eye, FIG. 5, shows a crescent at the top of the fundus reflex (see FIG. 5a).

The size of crescent is dependent upon three parameters: the subject to camera distance, the diameter of the pupils and the amount of the subject's refractive error. Research performed by Kari Kaakinen at 1 meter using the off-axis photorefraction technique while photographing a Carl Zeiss Jena demonstration eye, indicated a sensitivity of approximately $-2.0$ diopters for myopic and $+1.3$ diopters for hyperopic eyes.

H. C. Howland and B. Howland have demonstrated using a photorefractive attachment for a 35 mm camera, which used four 70 degrees pie-shaped cylinder-lens segments surrounded by a metal-clad tip of a fiber-optic light guide. This provided light on the camera lens and eye optic axis. The illumination of the image at the film plane can be computed for a perfectly diffusing retina and an aberration-free lens. Assume that the subject's eye is at a distance of (a) meters from the camera lens, that the diameter of his pupil is (p), and that the subject's refractive error is (E) diopters. The circle of light returned to the plane of the lens can be shown to have the diameter $$d = 2pEa$$

(This equation is also valid for a hyperopic eye or a normal eye focused E diopters beyond the camera plane.) Within this circle of reflected light, the illuminance (I) is given by the vignetting function of two coplaner circles of equal radii, namely, the circular pupil of the eye and the magnified retinal image of the probe as viewed from the camera. The following formula for the illuminance Ir shows this relationship:

$$I = (2/\pi) \arccos(r/r_b) - [(r/r_b)(1 - (r/r_b)^2)^{\frac{1}{2}}]$$

where (I) is the relative illuminance at any radius, (r), and ($r_b$) is the radius of the blur circle at the lens plane. This illuminance distribution is further transformed by the v-shaped, cylinder-lens segments, which collect more light from the periphery of the circle than from the center, which causes the formation of the lighter colored crescent at the top or bottom of the fundus reflex. The greater the diopter of refractive error, the longer the crescent area.

Figure 6B:
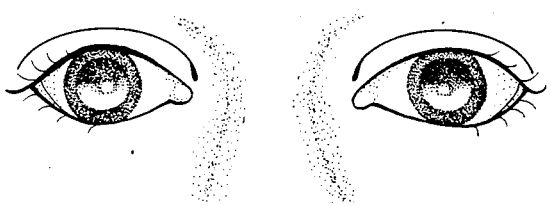
Figure 6C:
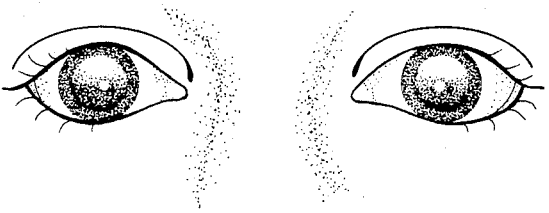
Figure 6D:
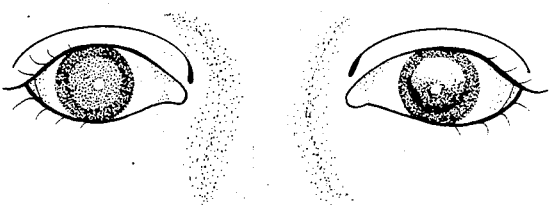
Figure 6E:
Figure 6F:
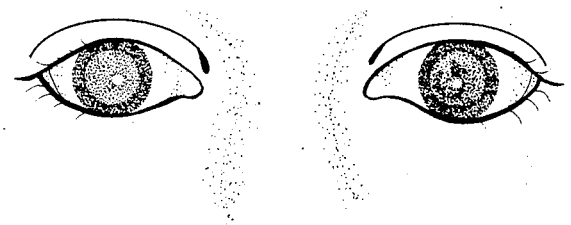
Figure 6G:
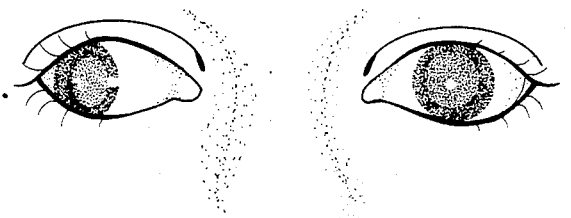

Looking now at FIGS. 6a to 6g, the figures show photographs which indicate various eye conditions, both normal and abnormal. FIG. 6a shows an emmetropic eye condition, which may be classed as "normal". Here, light rays entering the eye parallel to the optic axis pass through lens 41, and are brought to a focus exactly on the retina 43. FIG. 6b shows myopia, which is ordinarily called "nearsightedness". This is a condition in which rays of light entering the eye parallel to the optic axis are brought to a focus in front of the retina 43, as a result of the eyeball being too long from front to back. FIG. 6c shows hyperopia, which is ordinarily called "farsightedness." This is a condition in which rays of light are entering the eye parallel to the optic axis are brought to a focus in back of the retina 43, as a result of the eyeball being too short from back to front. FIG. 6d shows anisometropia, a general discrepancy between the refractive powers of the two eyes. FIG. 6e shows a fragmented retinal pattern of the eyes which also indicates refractive error. FIG. 6f shows a lens obstruction in one eye. FIG. 6g shows strabismus, a deviation of the eye which the patient cannot overcome. In this condition, the visual axes assume a position relative to each other which is different from that required by the physiological conditions.

The type of ametropic and non-ametropic ocular defects that are detected and illustrated in FIGS. 6a to 6g are listed in the table below:

| Emmetropic | Normal | FIG. 6a |
|---|---|---|
| Ametropic | | |
| Myopic | Nearsightedness | FIG. 6b |
| Hyperopic | Farsightedness | FIG. 6c |
| Anisometropic | Refractive error difference | FIG. 6d |
| Fragmented Retinal pattern | refractive error | FIG. 6e |
| Non-ametropic | | |
| Lens Obstruction | Cataract, tumor | FIG. 6f |
| Strabismus | Crosseyed | FIG. 6g |

The size of the crescent is dependent upon three parameters: (1) subject to camera distance, (2) the diameter of the pupils, and (3) the subject's refractive error. The subject to camera distance is fixed at 2.4 m. The pupil diameter is variable 4 mm to 10 mm because cycloplegic agents are not utilized. The system sensitivity is directly proportional to the pupil size. As pupil size increases, so does sensitivity. The threshold sensitivity of subjects with 8 mm diameter pupils is around $-0.25$ to $-0.50$ diopters of refractive error for myopes and $+0.50$ to $+0.75$ for hyperopes.

The present photorefractive ocular screening system has a number of advantages over the earlier photorefractive systems, which in general, were experimental and did not produce satisfactory results. The following are considered advantages of the present system, which is disclosed and claimed herein:

1. The system requires a room capable of providing only 12 feet of unobstructed floor space.

2. The system is quite portable; its mass is less than 10 kg and it folds up to a package less than 4 feet long. Minimum alignment is required after unfolding.

3. No assembly of the system is required to set it up; the camera station and head positioning station are an integral part of the hinged interconnect beam structure.

4. In the present system, corneal reflection is so minimal that it is not detrimental to the results produced by the system; the reflection obscures no more than 0.9% of the surface area of the retinal reflex image.

5. The image quality using a Tamron ®, f/8, 500 mm, tele-macro, catadioptric lens is excellent in terms of image size, resolution, and depth of field.

6. Refractive error indications produced by the present system are not exaggerated; the system sensitivity is $-0.25$ to $-0.50$ diopters for myopic errors and $+0.50$ to $+0.75$ diopters for hyperopic errors.

7. The 2.4 meter camera to subject distance is near the optimum distance for best all around results. A greater distance is impractical, while a lesser distance would decrease the depth of field, resulting in less image quality and significantly reduced sensitivity, especially for hyperopes.

From the above, it may be seen that the invention provides a method and apparatus for detecting eye defects which is simple, reliable, fast, and relatively inexpensive. The invention fulfills a long term need for a practical way to screen large numbers of population, particularly school children, to detect eye problems so that corrective action may be taken to improve their eyesight. Moreover, prevention of further deterioration of the eyes and prevention of eye diseases are possible for considerable numbers of persons.

What is claimed is:

1. An accurate photorefractor ocular screening apparatus for obtaining at the same time a photograph of both eyes of a person including the corneal reflection and the fundus reflex from both eyes, comprising:

a straight horizontal elongated beam of a plurality of meters in length;

an upright head positioning structure attached to said elongated beam contiguously to one end for positioning the head of a person whose eyes and reflection therefrom are being photographed;

an upright camera and flash unit structure attached to said elongated beam contiguously to the other end;

said head positioning structure having a hood to frame around both of said person's eyes and adjacent face segment;

said hood having a semicircular concave, cut-out to tightly fit around said person's face and an additional center cut-out to accommodate said person's nose;

said camera and flash unit structure having a camera with a lens adapted to focus on said person's eyes framed by said hood at a distance of approximately 2.4 meters, said optical axis of said camera being substantially parallel to said elongated beam, and said hood having its center line along said optical axis so that said person may look with both eyes through said hood toward the camera lens;

said camera and flash unit structure having a light flash unit located adjacent said camera and off-axis to said optical axis of said camera and facing said head positioning structure so as to flash illuminate said person's eyes and face segment framed by said hood when operated simultaneously with the film exposing operation of said camera, said flash illumination entering said person's eyes and passing through the eyes cornea and lens and striking the eyes retinas from which it is reflected back toward the camera lens together with the reflection of the flash illumination from the outer surfaces of the person's eyes; and a lamp means fixed on said head positioning structure below said hood that places light adjacent said person's nose and cheeks whereby when light is reflected upward past said person's nose and cheeks it may be observed through said hood by an operator facing said hood, thereby indicating improper positioning of said person's head; and an eye fixation light means fixed to said upright camera and flash unit structure and closely adjacent said camera lens to provide a fixation target upon which said person's eyes may focus, thus enabling a photograph to be taken substantially from the focus point of said person's eyes.

2. A screening apparatus according to claim 1 further comprising:

said elongated beam having sections hinged together which are adapted to be folded together whereby said screening apparatus is adapted to be folded in a compact position for storage and traveling by folding the sections of said elongated beam to lie flat against each other and thereby placing said head positioning structure and said camera and flash unit structure closely adjacent to each other.

3. A screening apparatus according to claim 1 further comprising:

said lamp means emit a color light to prevent said person's eyes from undilating.

4. A screening apparatus according to claim 1, further comprising:

said lens provides a large depth of field when focused at 2.4 meters.

5. A screening apparatus according to claim 1 further comprising:

said lamp means consists of two lamps positioned on either side of the head positioning structure.

6. A screening apparatus according to claim 1 further comprising:

said eye fixation light means in a blinking light.

* * * * *